(12) United States Patent
Barwacz

(10) Patent No.: US 8,708,091 B2
(45) Date of Patent: Apr. 29, 2014

(54) CORDED HEARING PROTECTIVE DEVICE AND METHOD OF MANUFACTURING THE SAME

(75) Inventor: Robert Franciszek Barwacz, Cracow (PL)

(73) Assignee: 3M Innovative Properties Company, St. Paul, MN (US)

( * ) Notice: Subject to any disclaimer, the term of this patent is extended or adjusted under 35 U.S.C. 154(b) by 480 days.

(21) Appl. No.: 10/282,280

(22) Filed: Oct. 28, 2002

(65) Prior Publication Data

US 2004/0079579 A1    Apr. 29, 2004

(51) Int. Cl.
*A61B 7/02* (2006.01)

(52) U.S. Cl.
USPC .......................................... 181/135

(58) Field of Classification Search
USPC .......... 181/129, 130, 135; 128/864, 867, 567; D24/106; D29/112; 289/1.2, 1.5
See application file for complete search history.

(56) References Cited

U.S. PATENT DOCUMENTS

| | | | | |
|---|---|---|---|---|
| 78,493 | A | * | 6/1868 | Stilwell .......................... 607/136 |
| 2,459,530 | A | * | 1/1949 | Johnston .......................... 289/17 |
| 3,729,892 | A | | 5/1973 | Aslund et al. |
| D241,881 | S | * | 10/1976 | Peterson et al. ............. D24/106 |
| 4,008,912 | A | * | 2/1977 | Kotov ............................. 289/1.2 |
| D245,202 | S | * | 7/1977 | Asker .......................... D24/106 |
| 4,053,051 | A | | 10/1977 | Brinkhoff |
| 4,193,396 | A | * | 3/1980 | Wacker .......................... 128/864 |
| 4,219,018 | A | * | 8/1980 | Draper, Jr. .................... 128/864 |
| 4,253,452 | A | * | 3/1981 | Powers et al. ................ 128/864 |
| 4,314,553 | A | * | 2/1982 | Westerdal ...................... 128/864 |
| D277,317 | S | * | 1/1985 | Eisenmenger ................ D24/106 |
| 4,711,476 | A | * | 12/1987 | Hanson .......................... 289/1.2 |
| 4,724,922 | A | * | 2/1988 | Kalayjian ...................... 181/135 |
| 4,806,186 | A | | 2/1989 | Sirkin |
| 4,881,616 | A | * | 11/1989 | Janssen et al. ................ 181/129 |
| 4,936,411 | A | * | 6/1990 | Leonard ........................ 181/135 |
| 5,541,677 | A | | 7/1996 | Huhtala |
| 5,557,077 | A | * | 9/1996 | Berg .............................. 181/135 |
| 5,581,821 | A | | 12/1996 | Nakano |
| 5,668,354 | A | | 9/1997 | Falco |
| 5,711,313 | A | * | 1/1998 | Fleming ........................ 128/864 |
| 5,799,658 | A | * | 9/1998 | Falco ............................. 128/864 |
| 6,440,339 | B1 | | 8/2002 | Magidson et al. |
| 6,619,703 | B2 | * | 9/2003 | Dirks et al. ..................... 289/1.2 |
| 2002/0124851 | A1 | * | 9/2002 | Knauer et al. ................ 128/864 |
| 2003/0029458 | A1 | | 2/2003 | Tlemens |

FOREIGN PATENT DOCUMENTS

| | | |
|---|---|---|
| EP | 0 244 979 | 11/1987 |
| EP | 0 244 979 | 9/1990 |
| EP | 0 386 220 | 9/1990 |
| WO | WO 90/01914 | 3/1990 |
| WO | WO 98/06362 | 2/1998 |
| WO | WO 02/43633 | 6/2002 |

OTHER PUBLICATIONS www.layhands.com/knots/Knots "The Most Useful Knots for the average person to know" updated Jun. 13, 2004.*

(Continued)

*Primary Examiner* — Forrest M Phillips
(74) *Attorney, Agent, or Firm* — Craig A. Deutsch

(57) ABSTRACT

A hearing protective device is provided including a first sound attenuating element, a second sound attenuating element, a flexible elongated member connecting the first sound attenuating element and the second sound attenuating element, and a knot formed in the flexible elongated member, the knot is untied by moving the first sound attenuating element in a direction away from second sound attenuating element.

16 Claims, 4 Drawing Sheets

(56) References Cited

OTHER PUBLICATIONS

"Cole-Parmer General Catalog 2002-2003" Online!2002, Cole-Parmer Instrument Comp, Retrieved from Internet: URL: http://www.coleparmer.com/catalog/product_list.asp?cls=7520&par=0,20250&cat=1&sch=604&sku=&sel=.*

Internationa Search Report; PCT/US03/32601; Sep. 9, 2004.

"Gehorschutz UVEX Programm 2000" Online! 2000, UVEX Arbeitsschutz GMBH, Wurzburg DE, XP002294381; Retrieved from the Internet: URL:http://www.uvex-safety.de/uvex/central/safety/resource.nsf/imgref/64317A98EA2A69CDC1256DE4003E118B/$FILE/Gehoerkatalog.pdf.

"Cole-Parmer General Catalog 2001-2002" Online! 2001, Cole-Parmer Instrument Comp, XP002294382; Retrieved from Internet: URL:http://www.coleparmer.com/catalog/file_redirect.asp?file=0102_pdf/U-1560.pdf;.../U-1561.pdf;.../U-1562.pdf>p. 1560-p. 1562.

* cited by examiner

US 8,708,091 B2

CORDED HEARING PROTECTIVE DEVICE AND METHOD OF MANUFACTURING THE SAME

BACKGROUND OF INVENTION (1) Field of Invention

The present invention relates generally to hearing protective devices, and more particularly to a hearing protective device including two attenuating elements connected by a knotted cord and a method of manufacturing the hearing protection device.

(2) Description of Related Art

The use of hearing protective and noise attenuating devices is well known, and various types of devices are available including, but not limited to, ear muffs, semi-aural devices, and earplugs. Earplugs are particularly preferred for their effectiveness in attenuating sound and for comfort properties provided thereby.

An earplug generally comprises a sound attenuating element which is placed in the ear canal of a wearer to provide desired sound attenuation. The sound attenuating element is commonly made of a resilient foam material or a flexible, rubber-like material.

Several types of earplugs are known. A roll-down type earplug typically has a resilient foam body which is rolled by a user to reduce a diameter thereof. A portion of the reduced diameter earplug body is then inserted in the ear canal and allowed to expand therein to fill the canal and provide desired attenuation. The remaining portion of the earplug body extends from the ear canal and provides a handle for removing the plug. A push-in stem type earplug, as shown for example in FIG. 7, includes a resilient body 2 having a rigid or semi-rigid stem 4 embedded therein and, most typically, extending therefrom. The stem provides a degree of rigidity to the earplug which facilitates insertion of the plug body into the ear canal. During use, the exposed stem portion of the push-in stem earplug extends from the ear canal, thus providing a handle for removal of the earplug.

Earplugs often include a cord that attaches a pair of plugs and extends therebetween. See FIG. 1 in which earplugs 10 are shown connected by a cord 12. The cord 12 allows a user to hang the earplugs around their neck or elsewhere when the plugs are not being used. Also, the cord permanently relates a certain pair of earplugs and prevents against loss thereof.

Conventional cords are commonly designed so that the cord may be permanently attached to the earplugs and more specifically, each end of the cord may be permanently attached to ends of the earplugs. In the case of roll-down type earplugs, a cord is attached to one end of the resilient body. Push-in stem type earplugs generally have the cord attached at the exposed portion of the stem. Cords may be attached to the various types of earplugs, for example, by sonic welding or by adhesive bonding.

Corded earplug pairs are often sold in individual packages. For example, a single pair of earplugs attached by a cord are enclosed in a small plastic sealed package. A user acquires the package and opens the same to access the corded earplug pair. In this way, an individual pair of earplugs is conveniently provided to a user while a sanitary condition of the plugs in the sealed package is maintained.

Several methods of assembling and packaging the corded earplug pairs are known. With reference to FIGS. 1-4, the cord 12 is first manufactured and then wound in a spiral fashion so as to form a circular shaped bundle 14. Then a plastic clip 16 may be applied to the cord bundle to retain the circular shape thereof. Particularly, the plastic clip 16 is similar, if not identical, to plastic clips commonly used to maintain closure of bread bags. Once the cord 12 is clipped, the bundle 14 is positioned for connection with the earplugs 10. The two ends of the cord 12 are each attached to respective ends of each of the earplugs 10. As mentioned above, attachment may be made through a welding or adhesive bonding process. The corded earplugs 10 with the clipped cord 12 are then inserted into a waiting package 18 and the package 18 is sealed. The package 18 is, for example, a small plastic bag having an opening 20.

During packaging of the corded plugs, the clip is kept fastened to the cord bundle to maintain a compactness thereof and to prevent the cord from unwinding during or prior to packaging. The more compact the cord bundle, the less packaging material is required thus reducing material costs. Compactness of the cord bundle during packaging is also advantageous in facilitating insertion of the bundle into the package, i.e. a tight, compact cord bundle is much easier to pass through the opening of the package then a loose or unraveling cord bundle.

However, the plastic clip used to maintain the compact cord bundle is itself a separate product which increases the overall cost of the packaged corded earplug pair. Additionally, use of the plastic clip necessitates an additional step in the corded earplug assembly and packaging process. Further, the clip occupies valuable space within the packaging, thus the package must be slightly oversized to accommodate the clip. Accordingly, waste and disposal of the packaged clipped earplug is significant considering the additional piece of the clip and the required size increase of the package. Finally, the clipped cord is inconvenient for an end user since the clip must be manually removed prior to donning the earplugs. Further, the removal of the clip may threaten the integrity of the cord in that the plastic clip may contain sharp edges which can score the cord upon removal.

Referring now with particularity to FIG. 3, a paper wrap 22 has also been used to retain the cord bundle 14 in place of the plastic clip 16. The paper wrap 22, which is similar to a shoestring wrap or a light tape material, is wrapped around the spiral wound cord bundle 14 to retain the compact circular shape thereof. Then, the earplugs 10 are fixed to respective ends of the wrapped cord 12 and the corded pair is inserted into the waiting package 18.

Similar to the plastic clip, the paper wrap facilitates packaging of the corded earplug pair by maintaining the cord in a tightly wound, compact form and preventing against unraveling of the cord during or prior to insertion of the cord into the package. However, as with the plastic clip, the paper wrap is an additional item which increases the overall cost of the packaged earplugs, necessitates an additional step in the assembly process of the corded plugs, and requires the end user to incur the inconvenience of removing the paper wrap prior to unraveling the cord. Further, the paper is an additional piece which must be discarded by the end user, thus raising environmental and disposal concerns.

Referring now particularly to FIG. 4, it has also been attempted to assemble and package corded earplug pairs without utilizing a cord retaining device such as the plastic clip or paper wrap discussed herein above. In such a process, the cord 12 is first wound in a spiral to form the circular shaped cord bundle 14. The frictional properties of the cord 12 material are relied upon to retain the cord 12 in this wound position. The wound cord bundle 14 is then inserted in a waiting package. However, the cord 12 does not consistently remain in the wound bundle position, often coming unwound during or just prior to insertion of the cord bundle into the package. Further, compactness of the cord bundle is not obtained in this process requiring a larger package, thus increasing associated costs and again raising disposal and environmental concerns.

Accordingly, there remains a need for a corded earplug pair which may be efficiently and economically assembled and packaged and which may be readily accessed and used by a user.

SUMMARY OF INVENTION

The above discussed and other problems and deficiencies of the prior art are overcome or alleviated by the hearing protective device and method of manufacture of the invention.

In one embodiment of the invention, a hearing protective device is provided, including a first sound attenuating element, a second sound attenuating element, a flexible elongated member connecting the first sound attenuating element and the second sound attenuating element, and a knot formed in the flexible elongated member. The knot is untied by moving the first sound attenuating element in a direction away from second sound attenuating element.

In a further embodiment of the invention, a method of manufacturing a hearing protective device is provided including forming a first sound attenuating element, forming a second sound attenuating element, forming a flexible elongated member, tying a knot in the flexible elongated member so as to position the flexible elongated member in a wound bundle including first and second opposite ends extending from the bundle, and attaching the first and second opposite ends to the first and second sound attenuating elements, respectively.

The above discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES.

DETAILED DESCRIPTION OF INVENTION

Figure 1:
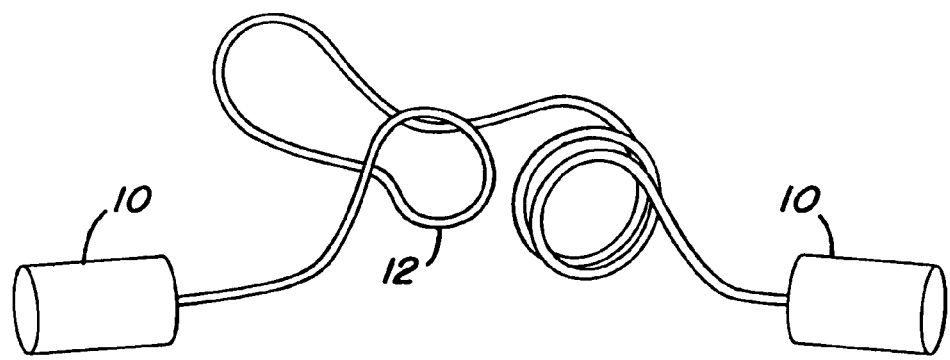
FIG. 1 is perspective view of a corded hearing protective device.
Figure 2:
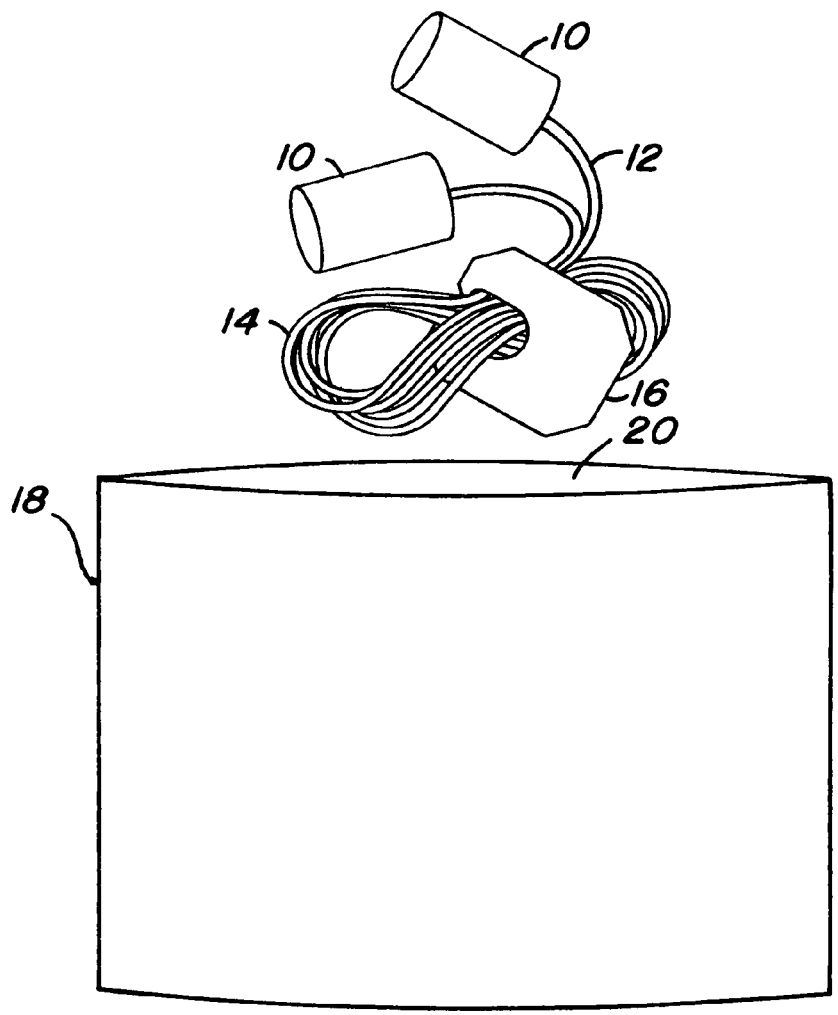
FIG. 2 is a perspective view of the hearing protective device in a wound and clipped position.
Figure 3:
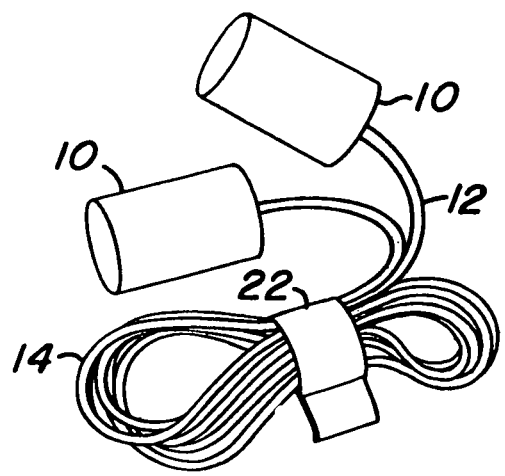
FIG. 3 is a perspective view of the hearing protective device in a wound and taped position.
Figure 4:
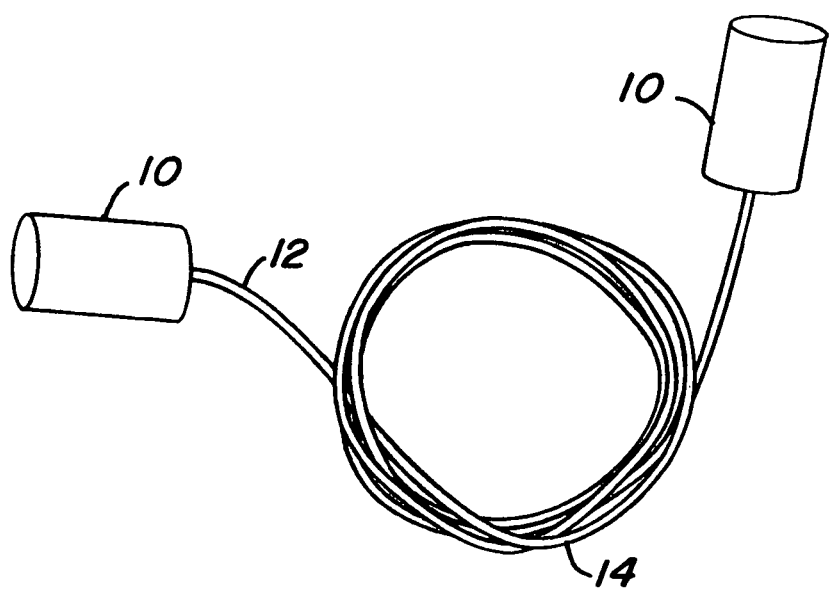
FIG. 4 is a perspective view of the hearing protective device in a wound position.
Figure 5:
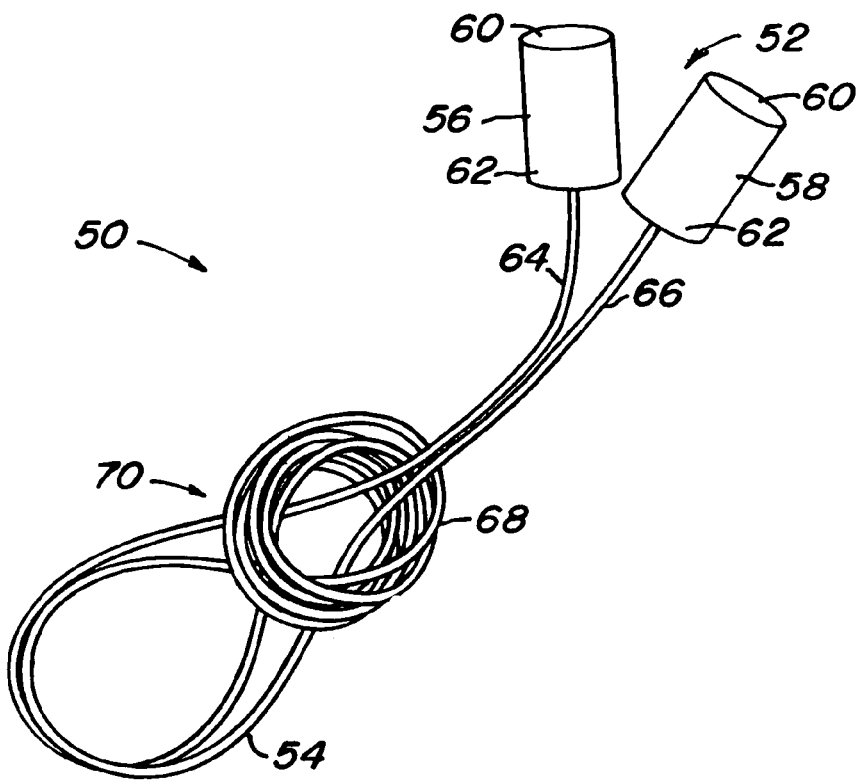
FIG. 5 is a corded hearing protective device according to the invention.

FIG. 5 shows a hearing protective device 50 including attenuating elements 52 connected by a cord 54.

In an exemplary embodiment, the attenuating elements 52 comprise a first earplug 56 and a second earplug 58. The first and second earplugs 56 and 58 each include a first end 60 and a second end 62 disposed opposite one another. One of the first and second ends 60 and 62 is attached to the cord and the other end is designated for insertion and retention in an ear canal of a user. In one embodiment, the second end 62 is attached to the cord and the first end 60 extends therefrom and is insertable and retainable in the ear canal. The second end 62 also serves as a handle for adjusting and removing the inserted earplug, and provides an attachment portion at which the cord is fixed.

Figure 7:
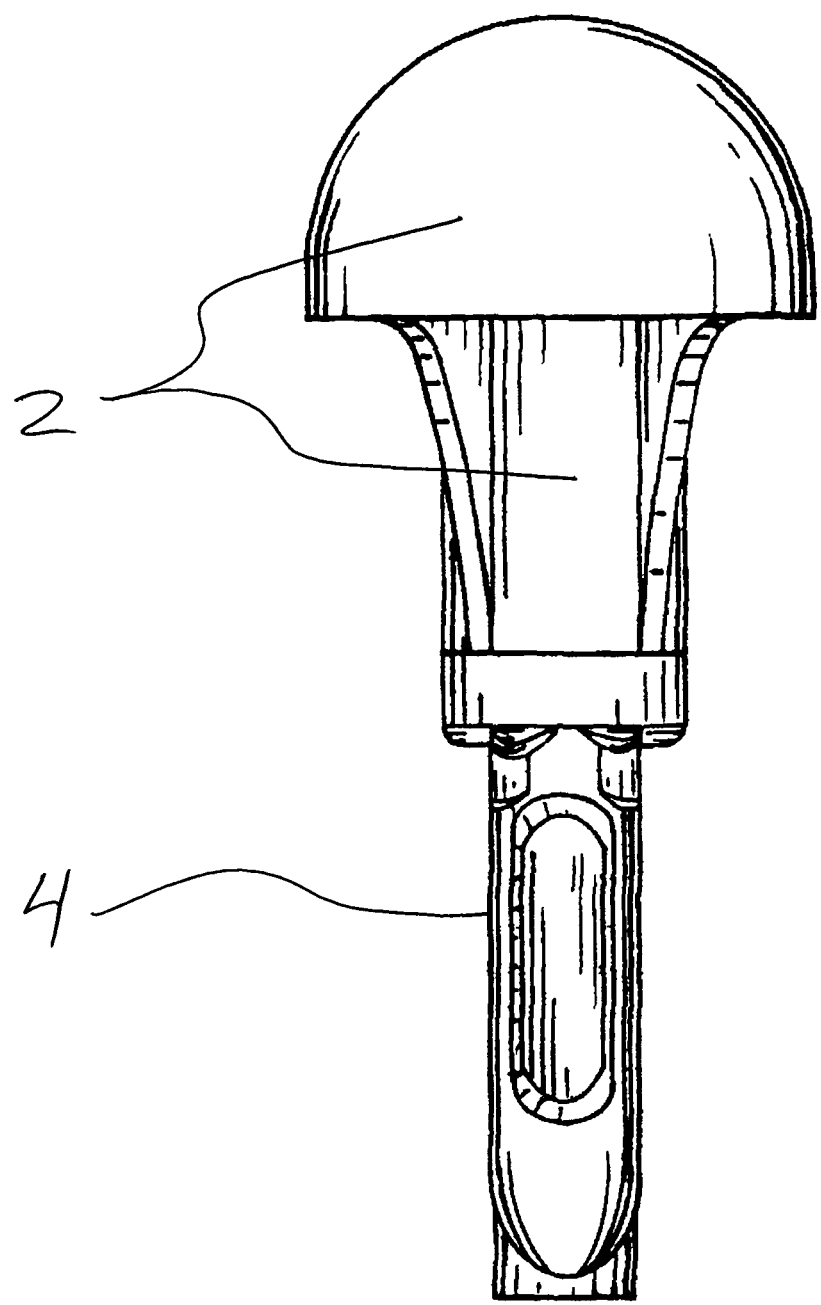
FIG. 7 is an enlarged view of a stemmed earplug.

The earplugs 56 and 58 may be of any desired style and/or construction. For example, the earplugs may be roll-down type resilient foam earplugs, push-in stem type earplugs (as shown, for example, in FIG. 7), pre-molded polymeric flange type earplugs, or any other desired type of earplug.

The cord 54 is composed of a rubber or plastic material and may be of a solid construction or, alternatively, may have a hollow portion at an interior thereof. The cord 54, of course may be of any material suitable for attaching the two earplugs including, for example, string, cotton material, vinyl, etc. The cord 54 includes a first end 64 and an oppositely disposed second end 66. The first end 64 of the cord 54 is attached to the first earplug 56 at the attachment end 62. Similarly, the second end of the cord 54 is attached to the second earplug 58 at the attachment end 62. The cord 54 is attached to the earplugs 56 and 58, for example, by sonic welding, adhesive bonding, mechanical bonding, etc.

The cord 54 includes a knot 68 formed therein. The knot 68 retains the cord 54 in a bundle 70. The bundle 70 is a compact generally curvilinear assembly of the cord 54 for facilitating handling and packaging of the hearing protective device 50. In one embodiment, the first and second cord ends 64 and 66 are maintained proximate one another in the bundle 70. The cord 54 forms a loop opposite the first and second cord ends 64 and 66, in the bundle 70, and the knot 68 is disposed therebetween.

The knot 68 generally comprises the cord 54 wound and/or wrapped in any manner so as to result in the bundle 70. The knot 68, in one embodiment, is a slip knot. A slip knot, for purposes of this application, is any knot which may be formed in an elongated member having two opposing ends where the knot may be untied by simply applying opposing forces to the opposing ends of the elongated member.

With respect to the hearing protective device 50, this means that the knot 68 is formed such that the knot 68 may be untied and the cord 54 correspondingly unraveled by a user simply pulling in opposite directions on the first and second earplugs 56 and 58 respectively attached to the first and second ends 64 and 66 of the cord 54. While being easily untied by a user, the knot 68 still supplies sufficient retention properties to maintain the cord 54 in the tight bundle 70 configuration. In this embodiment, the slip-knot type knot 68 may be formed by winding a mid-portion of the cord 54 in a circular manner and passing the first and second ends 64 and 66 of the cord 54 through an open center of the circularly wound cord 54, thus forming the bundle 70. The bundle 70 is unraveled by a user simply pulling oppositely on the earplugs 56 and 58. Of course, the slip-knot type knot 68 may be formed in any other suitable manner so as to form and maintain the bundle 70 and so as to be easily untied by the user.

While the knot 68 has thus far been described as a slip knot, the invention contemplates any type of knot which is suitable for forming the bundle 70 and which may be easily untied, and the cord 54 correspondingly unraveled, by the user.

The knot 68, as mentioned, retains and maintains the cord 54 in the bundle 70. The bundle 70 is easily and conveniently insertable in an opening 72 of a package 74. The package 74 may be of a plastic material and, once the bundle 70 is inserted therein, the package 74 may be sealed for sale or distribution.

Figure 6:
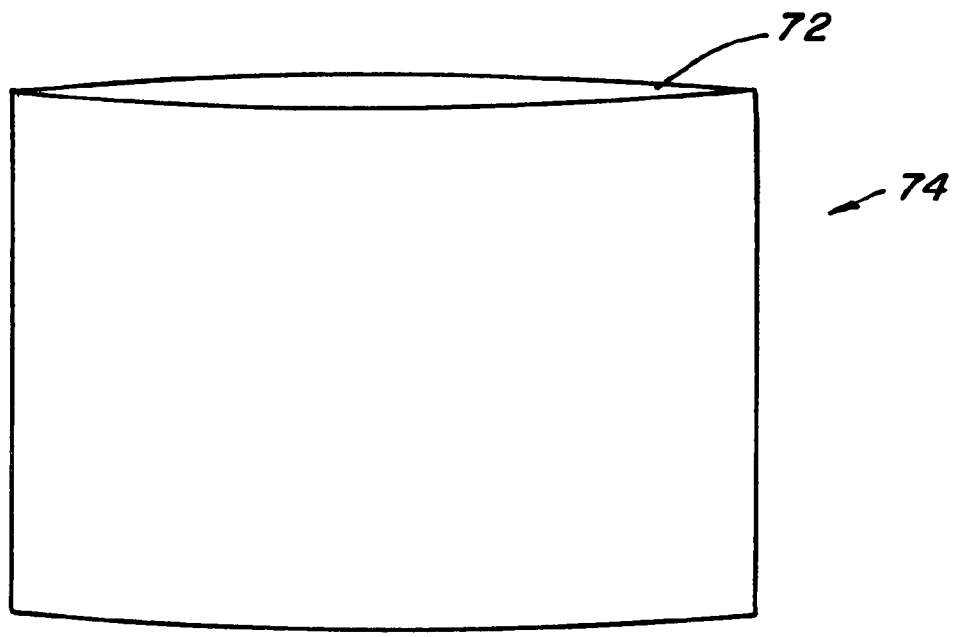
FIG. 6 is a depiction of a package for containing the corded hearing protective device.

A method of manufacturing the hearing protective device 50 is now described. First, the attenuating elements 52 and the cord 54 are separately formed. Then, the knot 68 is tied in the cord 54, thus forming the bundle 70. Next, the attenuating elements 52 are fixably attached the exposed first and second ends 64 and 66 of the cord 54. The corded and knotted hearing protective device 50 is then inserted through the opening 72 into the package 74. See FIG. 6. The opening 72 is closed and the package 74 is sealed.

The corded hearing protective device of the invention may be efficiently and economically assembled and packaged so as to be readily accessed and used by a user. The knot in the cord forms a tight, compact, and manageable cord bundle to which attenuating elements may be readily attached. The knot ensures that the cord is held in the bundle, the bundle being of a reduced size, thus simplifying the packaging process while minimizing necessary packaging materials. The knotted cord of the invention does not require additional clips, paper wrap, tape, etc. to maintain the cord in the bundle. Thus, the invention satiates environmental and disposal concerns by producing less waste since no clip or tape members are required and yet a small package may still be utilized. Additionally, the knot is easily untied thus facilitating a user's access to the corded hearing protective device. In one embodiment, a slip knot is used such that the user may simply pull in opposite directions on the sound attenuating elements to untie the knot, unraveling the cord and thus accessing the hearing protective device.

While preferred embodiments have been shown and described, various modifications and substitutions may be made thereto without departing from the spirit and scope of the invention. Accordingly, it is to be understood that the present invention has been described by way of illustrations and not limitation.

The invention claimed is:

1. A hearing protective device, comprising:
a first sound attenuating element;
a second sound attenuating element;
a flexible elongated member connecting the first sound attenuating element and the second sound attenuating element, and
a knot formed in the flexible elongated member;
wherein the elongated member includes opposite first and second ends, and the knot comprises a circularly wound mid-portion having more than two circular windings, the first and second ends of the elongated member each forming a loop on one side of the circularly wound mid-portion and passing through a center of the circularly wound mid-portion to extend freely therefrom, and wherein the knot is untied and the circular windings unraveled by moving the first and second sound attenuating elements in a direction away from each other.

2. The hearing protective device of claim 1, wherein no additional parts are needed to maintain the circular windings of the flexible elongated member.

3. The hearing protective device of claim 1, wherein the first and second sound attenuating elements comprise earplugs.

4. The hearing protective device of claim 3, wherein each earplug comprises a resilient foam body including first and second opposite ends, the first end for being inserted into an ear canal of a user and the second end being attached to the flexible elongated member.

5. The hearing protective device of claim 3, wherein each earplug comprises a foam element fixed to a stem, the stem extending from the foam element, the cord being attached to the stem.

6. The hearing protective device of claim 3, wherein each earplug comprises a pre-molded body of a resilient polymeric material.

7. The hearing protective device of claim 6, wherein the body comprises a stem portion and a plurality of radially extending flange elements disposed on the stem portion.

8. The hearing protective device of claim 7, wherein the flange elements include substantially circular cross-sections and extend from the stem portion in a direction toward a rear of said stem portion to form an annular space between the flanges and the stem portion.

9. The hearing protective device of claim 1, wherein the flexible elongated member comprises a cord of a plastic material.

10. The hearing protective device of claim 1, wherein the knot is a slip knot.

11. A method of manufacturing a hearing protective device, comprising:
providing a first sound attenuating element;
providing a second sound attenuating element;
providing a flexible elongated member;
attaching the first and second sound attenuating elements to opposing ends of the flexible elongated member; and
tying a slip knot in the flexible elongated member;
wherein the elongated member includes opposite first and second ends, and the knot comprises a circularly wound mid-portion having more than two circular windings, the first and second ends of the elongated member each forming a loop on one side of the circularly wound mid-portion and passing through a center of the circularly wound mid-portion to extend freely therefrom, so as to allow for untying of the knot and unraveling of the circular windings by moving the first sound attenuating element in a direction away from the second sound attenuating element.

12. The method of claim 11, further comprising disposing the flexible elongated member with attached first and second attenuating elements in a package and sealing the package.

13. The method of claim 11, wherein the first and second sound attenuating elements comprise resilient foam earplugs formed by a molding process and the flexible elongated member comprises a cord of a plastic material.

14. The method claim 11, wherein the untying of the knot is such that, the elongated member is unraveled and the hearing protection device is prepared to he worn by a user.

15. The method of claim 11, wherein said attaching the first and second opposite ends comprises sonically welding the first and second attenuating elements to the first and second opposite ends, respectively.

16. The method of claim 11, wherein said attaching the first and second opposite ends comprises adhesively bonding the first and second attenuating elements to the first and second opposite ends, respectively.

* * * * *

UNITED STATES PATENT AND TRADEMARK OFFICE
CERTIFICATE OF CORRECTION

PATENT NO. : 8,708,091 B2  Page 1 of 1
APPLICATION NO. : 10/282280
DATED : April 29, 2014
INVENTOR(S) : Robert Barwacz It is certified that error appears in the above-identified patent and that said Letters Patent is hereby corrected as shown below:

On Title Page 2, Column 1, Item (56) Other Publications
Line 5, delete "Internationa" and insert -- International --, therefor In the Claims
Column 6
Line 48, in Claim 14, delete "method" and insert -- method of --, therefor.
Line 50, in Claim 14, delete "he" and insert -- be --, therefor.

Signed and Sealed this
Fifth Day of August, 2014

Michelle K. Lee
*Deputy Director of the United States Patent and Trademark Office*